US012263491B2

United States Patent
Jentsch

(10) Patent No.: US 12,263,491 B2
(45) Date of Patent: Apr. 1, 2025

(54) BLOOD-SEPARATION DEVICE WITH DISPLACEMENT BODY

(71) Applicant: LMB Technologie GmbH, Schwaig (DE)

(72) Inventor: Klaus Jentsch, Schwaig (DE)

(73) Assignee: LMB Technologie GmbH, Schwaig (DE)

( * ) Notice: Subject to any disclaimer, the term of this patent is extended or adjusted under 35 U.S.C. 154(b) by 755 days.

(21) Appl. No.: 17/601,620

(22) PCT Filed: Apr. 9, 2020

(86) PCT No.: PCT/EP2020/060212
§ 371 (c)(1),
(2) Date: Oct. 5, 2021

(87) PCT Pub. No.: WO2020/208166
PCT Pub. Date: Oct. 15, 2020

(65) Prior Publication Data
US 2022/0203380 A1    Jun. 30, 2022

(30) Foreign Application Priority Data
Apr. 12, 2019   (DE) .................... 10 2019 109 749.5

(51) Int. Cl.
*B04B 5/04*     (2006.01)
*A61M 1/02*     (2006.01)
*A61M 1/36*     (2006.01)

(52) U.S. Cl.
CPC ......... *B04B 5/0428* (2013.01); *A61M 1/0209* (2013.01); *A61M 1/3693* (2013.01); *A61M 2202/0413* (2013.01); *A61M 2205/33* (2013.01)

(58) Field of Classification Search
CPC . B04B 5/0428; A61M 1/0209; A61M 1/3693; A61M 2202/0413; A61M 2205/33
See application file for complete search history.

(56) References Cited

U.S. PATENT DOCUMENTS 4,608,178 A * 8/1986 Johansson ............. A61M 1/029
210/744
2002/0151423 A1   10/2002  Jorgensen et al.
(Continued)

FOREIGN PATENT DOCUMENTS

CA      2989898 C  *  1/2024 ............ A61M 1/362
CN    108578801 A      9/2018
(Continued)

OTHER PUBLICATIONS

Search Report received in International Application No. PCT/EP2020/060212 dated Jun. 29, 2020, with translation, 5 pages.
(Continued)

*Primary Examiner* — Walter D. Griffin
*Assistant Examiner* — Shuyi S. Liu
(74) *Attorney, Agent, or Firm* — Christopher A. Rothe; CM Law

(57) ABSTRACT

A device for separating blood into a plurality of blood components by centrifugal force includes a first chamber for receiving a blood bag filled with blood to be separated. Each separated blood component is located in a separate portion of the blood bag according to its specific weight. A second chamber receives at least one component bag to be filled with a blood component. The component bag has an inlet opening connected to an outlet opening of the blood bag by a line that has a controllable valve. A displacement body in the first chamber exerts a pressing force onto the blood bag. A control unit opens the valve until a blood component passes into the component bag as a result of the pressing force. The displacement body generates the pressing force (Continued)

with the aid of the centrifugal force and/or with the aid of a spring force.

16 Claims, 13 Drawing Sheets

(56) References Cited

U.S. PATENT DOCUMENTS

| | | | | |
|---|---|---|---|---|
| 2006/0122048 A1* | 6/2006 | Hlavinka | ............ | A61M 1/0209 |
| | | | | 494/84 |
| 2010/0170858 A1* | 7/2010 | Eberle | ................ | A61M 1/3698 |
| | | | | 210/381 |
| 2012/0289926 A1 | 11/2012 | Hirabuki et al. | | |
| 2016/0016173 A1 | 1/2016 | Eberle et al. | | |
| 2017/0176479 A1* | 6/2017 | Lüdicke | ............. | G06F 3/04847 |
| 2018/0154054 A1* | 6/2018 | Salomon | ............ | A61M 1/0281 |

FOREIGN PATENT DOCUMENTS

| | | | |
|---|---|---|---|
| DE | 2938367 A1 | 6/1981 |
| JP | 2016518971 A | 6/2016 |
| WO | 9200145 A1 | 1/1992 |

OTHER PUBLICATIONS

Office Action received in Japanese Application No. 2021-560616 dated Dec. 20, 2023, with translation, 3 pages.
Written Opinion received in International Application No. PCT/EP2020/060212 dated Jun. 29, 2020, with translation, 10 pages.
Search Report received in German Application No. 20 2019 104 978.2 dated Feb. 20, 2020, with translation, 10 pages.

* cited by examiner

BLOOD-SEPARATION DEVICE WITH DISPLACEMENT BODY

CROSS-REFERENCE TO RELATED APPLICATIONS

This application is the United States national phase entry of International Application No. PCT/EP2020/060212, filed Apr. 9, 2020, and claims the benefit of priority of German Application No. 10 2019 109 749.5, filed Apr. 12, 2019. The contents of International Application No. PCT/EP2020/060212 and German Application No. 10 2019 109 749.5 are incorporated by reference herein in their entireties.

FIELD

The present invention relates to a blood separation device for separating blood under the influence of a centrifugal force generated during a centrifugation process in a centrifuge. In particular, the present invention relates to a blood separation device in which the blood components are in separate containers after the centrifugation process.

BACKGROUND

It is known that blood taken up in a blood bag is separated into individual components according to the specific weight of the components, in the direction of the centrifugal force, under the influence of a centrifugal force that is generated during a centrifugation process. It is then necessary to transfer each of the individual components into a container provided for this purpose, so that the blood components are individually available for examinations and/or therapeutic purposes.

In conventional working methods, the blood is therefore first centrifuged, so that so that the individual blood components are separated into layers in the blood bag. The blood bag and associated component bags are then removed from the centrifuge and inserted into a separate blood separation device where blood components are transferred from the blood bag to the component bags. However, this procedure requires several time-consuming steps so that using the separate blood separation device, the individual blood components once again mix in the time between the centrifugation and the transfer to the component bags provided for this purpose.

For this reason, working methods are known of from the prior art, e.g. DE 29 38 367 A1, in which the blood is separated into the individual blood components during a centrifugation process in the blood bag. Subsequently, when the centrifuge rotor peters out, the individual blood components are displaced from the blood bag with the help of compressed air or hydraulic pressure, so that the components are each transferred via a line into one or more satellite bags.

However, to carry out this working method, a special centrifuge is required which provides a compressed air connection or a hydraulic line for a receiving container in the centrifuge and/or a centrifuge basket into which the blood bag containing the blood to be separated is inserted. Compared to centrifuges that are only used to separate the blood, the construction of such a centrifuge requires greater technical effort, which leads to high procurement costs for these centrifuges.

SUMMARY

The object of the present invention is to provide an inexpensive and easy-to-use blood separation device. The blood separation device in accordance with the invention should be especially applicable with conventional centrifuges which do not have a compressed air connection or hydraulic connection. Consequently, it is possible to avoid the technical effort as well as the high costs for the procurement of a new centrifuge.

In accordance with one aspect of the present invention, the blood separation device is configured to displace the individual blood components from the blood bag by a displacement body which is shaped to generate a pressing force that is substantially perpendicular to the centrifugal force by means of a centrifugal force which is generated during a centrifugation process and/or by means of a spring force. The individual blood components then pass into corresponding component bags, wherein an inlet opening of each component bag is connected to an outlet opening of the blood bag via a line in which a controllable valve is arranged. The blood separation device according to the invention further comprises a control unit which, after the completion of a first phase of the centrifugation process in which the blood is separated into the individual blood components, opens each valve until the blood component associated with that valve has passed into the associated component bag as a result of displacement by means of the pressing force generated by the displacement body.

The transfer of the individual blood components into the corresponding component bags is therefore carried out during a second phase of the centrifugation process. The centrifugal force during the second phase is smaller than the centrifugal force during the first phase. Preferably, the second phase is a phase in which the centrifuge is adjusted to apply a predetermined centrifugal force. Alternatively, the second phase can be a petering out of a centrifuge rotor.

It should be noted that a pressing force generated by means of the spring force already presses on the blood bag when the blood bag is inserted into the blood separation device. However, by opening and closing the valves in the lines from the blood bag to the component bags controlled by a control unit, the flow of the individual blood components to the corresponding component bags can be specifically influenced, so that it is not necessary to apply the pressing force, as described in DE 29 38 367 A1, after the blood has been separated into the individual blood components.

BRIEF DESCRIPTION OF THE DRAWING FIGURES

In the following description, modifications of the blood separation device in accordance with the invention as well as different embodiments for separating the individual blood components are described with reference to the attached figures. The following section describes the figures.

Figure 13A:
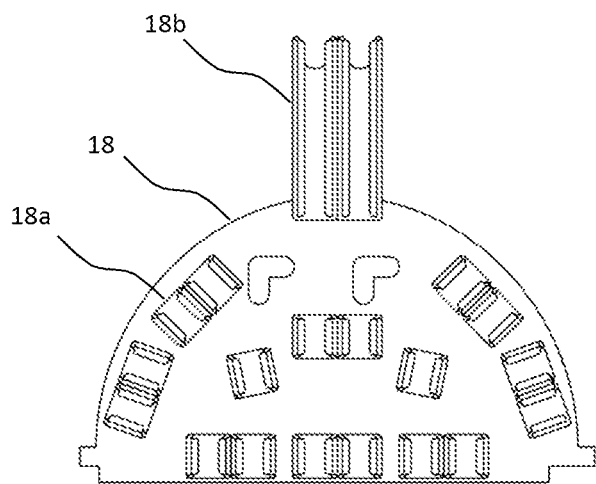
Figure 13B:
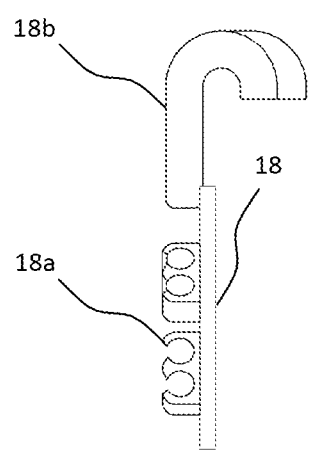
Figure 14:
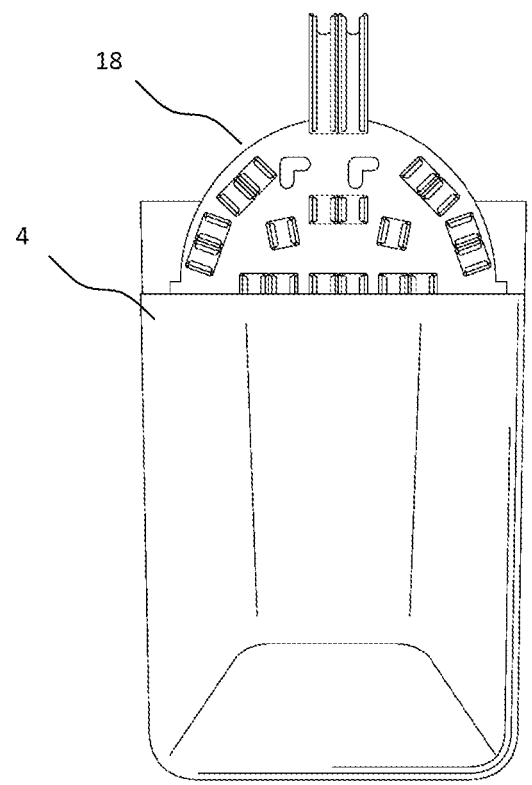

FIGS. 13A and 13B respectively show front and side views of a guide plate in order to guide lines between the blood bag and the component bags; and FIG. 14 shows a side view of a blood separation device to which the guide plate is attached.

DETAILED DESCRIPTION

The blood separation device 4 in accordance with the invention can be realized using different modifications. For this reason, the different modifications will be described first of all. The different embodiments for using the blood separation device 4 will be explained in accordance with the invention in a later section of the description. It should be noted that the different embodiments can be implemented with all of the modifications of the blood separation device 4.

Figure 1:
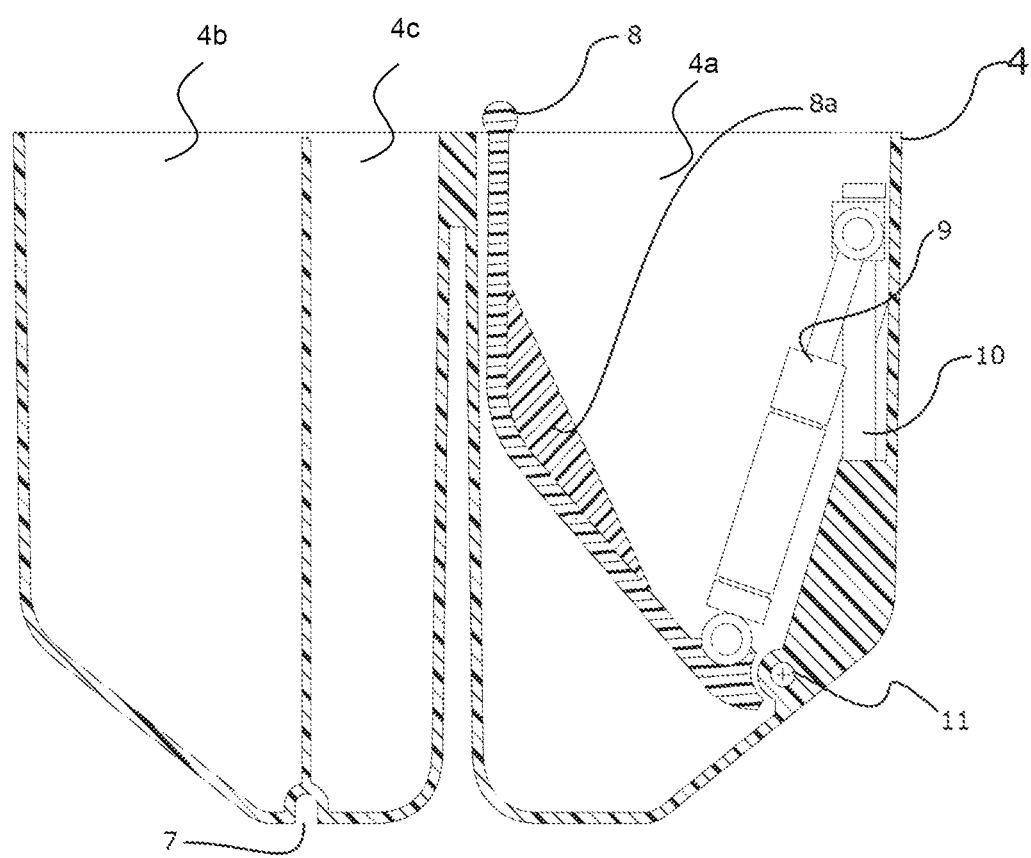
FIG. 1 shows a modification of a blood separation device.
Figure 2:
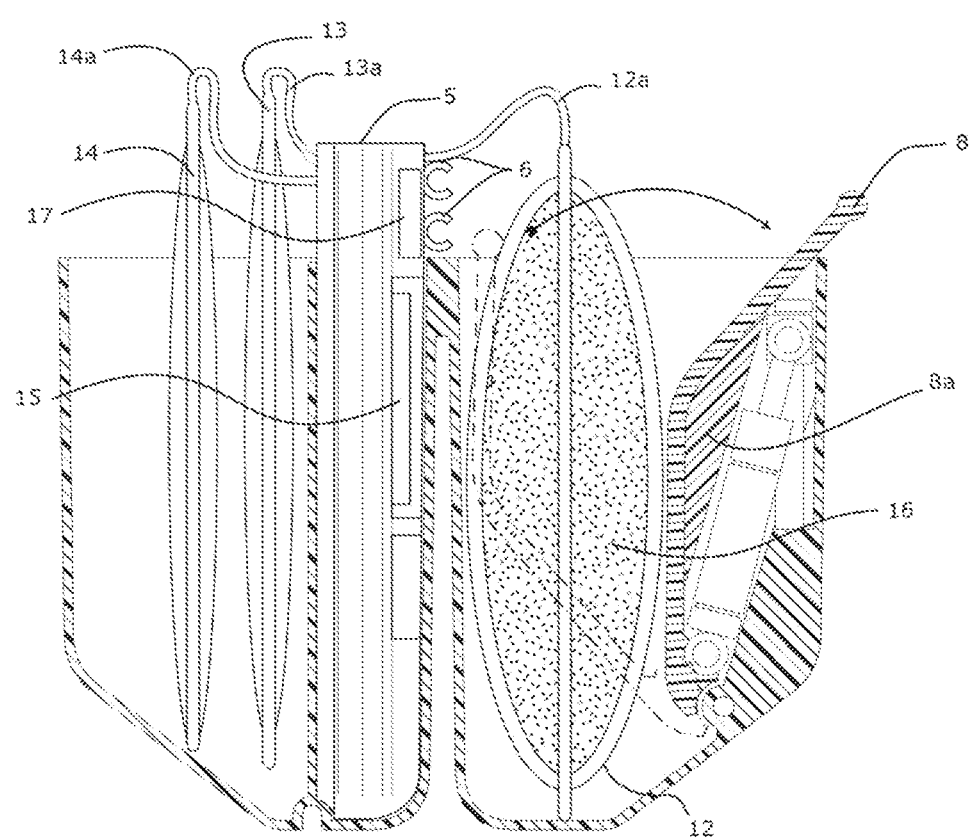
FIG. 2 shows the modification of the blood separation device, in which a control unit as well as a blood bag and two component bags are inserted, when used in accordance with an embodiment.

FIG. 1 and FIG. 2 show the structure of a blood separation device 4 in accordance with a modification. The blood separation device 4 has a first chamber 4a, a second chamber 4b and a chamber 4c for a control unit 5. A displacement body 8 is arranged in the first chamber 4a, which has a lever arrangement that is rotatably mounted on a wall of the first chamber 4a on an axis of rotation 11. The wall is, as can be seen in the figures, a wall of the first chamber, facing the exterior of the blood separation device 4. The displacement body 8 is arranged in order to generate a pressing force Fp, as shown for example in FIG. 4, so that the individual blood components 16a, 16b and 16c can be pressed out of the blood bag 12 and pass into respective component bags 13 and 14.

In this modification, the displacement body 8 is shaped to generate the pressing force Fp by means of a centrifugal force Fz that is generated during centrifugation and by means of a spring force Ff.

In order to generate the pressing force Fp by means of the centrifugal force Fz, the lever arrangement of the displacement body 8 has a weight 8a, the centre of gravity of which, as can be seen in FIG. 2, is arranged so that it is offset to a y-axis direction running vertically through the axis of rotation 11 in the direction of the second chamber 4b, i.e. in the figures, to the left. As a result, the centrifugal force Fz causes a counter-clockwise torque on the lever arrangement of the displacement body 8, pushing the lever arrangement of the displacement body 8 towards the second chamber 4b. An upper portion of the lever arrangement which is angled at a predetermined angle, such as 45°, to the lower portion of the lever arrangement in the direction of an outer face of the blood separation direction is pressed towards the opposite wall due to the rotation and is substantially parallel to an inside wall of the first chamber 4a. An upper portion therefore distributes the pressing force Fp generated by the centrifugal force Fz over a larger area of the inner wall of the first chamber 4a. In addition, this angled design of the lever arm provides the advantage that the lower section of the lever arm can be rotated further to the left, which increases the applied torque, as the weight 8a of the displacement body 8 is shifted further to the left with respect to the y-axis direction running vertically through the axis of rotation 11.

In addition, the blood separation device 4 in accordance with this modification has a spring 9, one end of which is attached to the wall of the first chamber 4a and the other end of which is attached to the displacement body 8 so that a spring force Ff of the spring generates a pressing force Fp which is substantially in the same direction as the pressing force Fp generated by means of the centrifugal force Fz. The spring force of the spring 9 can preferably be adjusted by means of a guide rail 10 by changing the travel of the spring by moving the end of the spring 9 attached thereto. If the attached end of the spring 9 is moved upwards, the travel of the spring is shortened and the spring force Ff decreases. If the attached end of the spring 9 is moved downwards, the spring travel is lengthened and the spring force Ff increases.

Consequently, the resulting pressing force Fp pressing on the blood bag 12 is the sum of the pressing force Fp generated by means of the centrifugal force Fz and the pressing force Fp generated by means of the spring force Ff. As such, in a state in which no blood bag 12 is accommodated in the first chamber 4a, the displacement body 8 is pressed against the inner wall of the first chamber 4a, as shown in FIG. 1 and dashed in FIG. 2.

The blood separation device 4 in accordance with another modification (not shown in the figures) does not have a weight 8a on the lever arrangement of the displacement body 8. Consequently, the pressing force Fp is generated almost exclusively by the spring force Ff of spring 9. It is only the centrifugal force Fz, which acts on the mass of the lever assembly itself, that generates a negligible pressing force Fp. In this case, the spring force Ff is to be designed by designing the spring itself or by moving one end on the guide rail 10 in such a way that the pressing force Fp generated by the spring force Ff, which consequently corresponds to the total pressing force Fp that is generated, is sufficient for the individual blood components 16a, 16b and 16c to be pressed out of the blood bag 12 and enter the component bags 13 and 14 provided for this purpose via the corresponding lines 13a, 14a. In this modification, the displacement body 8 is also pressed against the inner wall of the first chamber 4a due to the spring force Ff of the spring 9, similar to FIG. 1.

Figure 6:
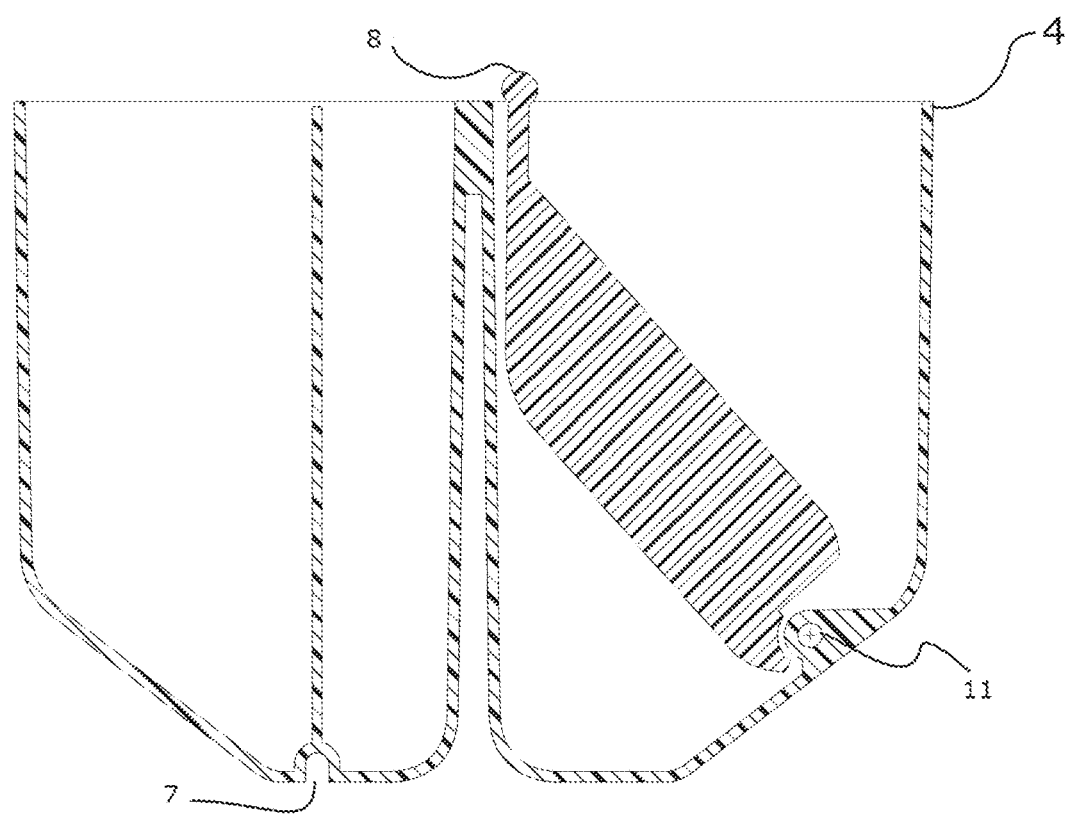
FIG. 6 shows a further modification of a blood separation device.

The blood separation device 4 in accordance with a further modification is shown in FIG. 6 and generates the required pressing force Fp exclusively with the aid of the centrifugal force Fz generated during centrifugation. For this reason, the displacement body 8 in accordance with this modification has a greater mass than the displacement body 8 in accordance with the modifications described above, so that the pressing force Fp generated with the aid of the centrifugal force Fz, which consequently corresponds to the total pressing force Fp that is generated, is sufficient to press the individual blood components 16a, 16b and 16c out of the blood bag 12. The mass of the lever arrangement is distributed on the displacement body 8 in such a way that the centre of gravity of the displacement body is shifted to the left in relation to a y-axis direction running vertically through the axis of rotation 11. As a result, the displacement body 8 is deflected in the direction of the inner wall of the first chamber 4a in an initial state, as shown dashed in FIG. 6 and in FIG. 7.

This weight distribution and the resulting centre of gravity shifted to the left ensure that, under the influence of the centrifugal force Fz that is generated, a torque acts on the lever arrangement of the displacement body 8 which is directed counter-clockwise. Consequently, the pressing force Fp is generated, which presses in the direction of the inner wall of the first chamber 4a. As in the previously described modifications, an upper portion of the lever arrangement of the displacement body 8 is angled towards the outer face of the blood separation direction at a predetermined angle. This way, the pressing force Fp is also distributed over a larger area and a lower section of the displacement body 8 can be deflected further to the left.

Figure 12A:
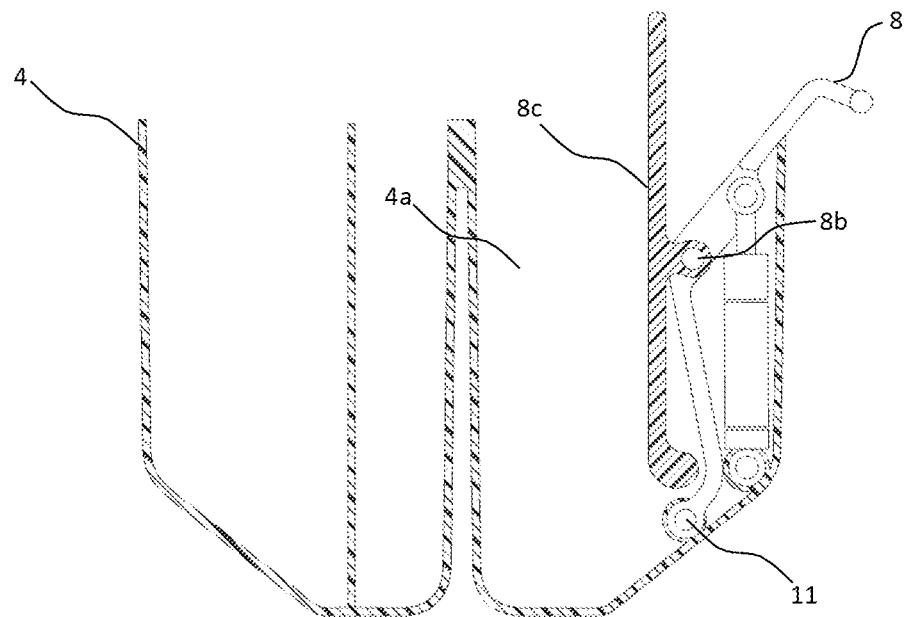
FIG. 12A and FIG. 12B show a further modification of the blood separation device in which a displacement body comprising of a lever arrangement with a gimbal bearing and a pressure plate is used.
Figure 12B:
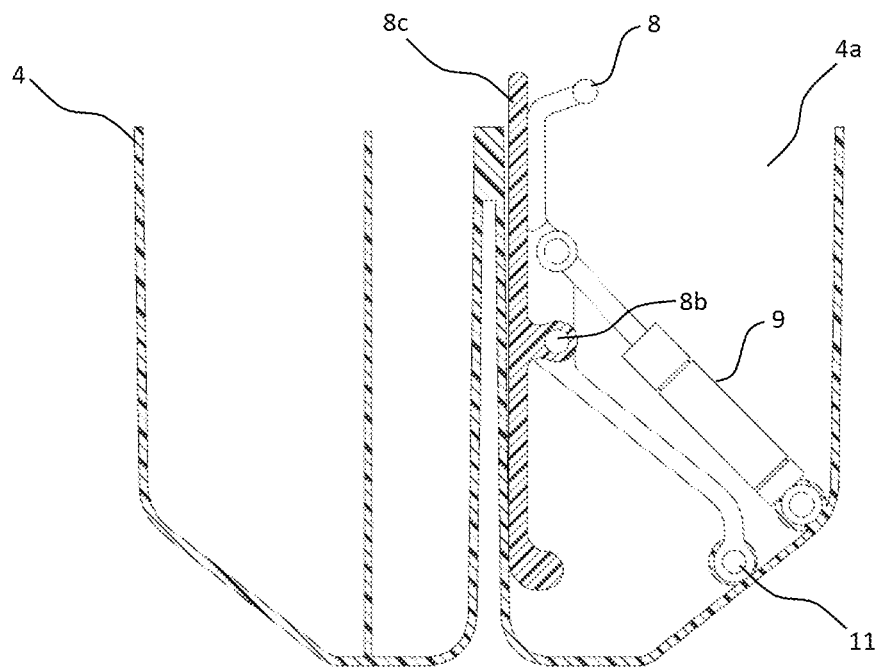

In accordance with another modification shown in FIGS. 12A and 12B, the displacement body 8 may comprise a lever arrangement to which a gimbal bearing 8b and a pressure plate 8c are attached. The gimbal bearing 8b ensures that the pressure plate 8c is arranged parallel to the inner wall of the first chamber 4a. By using the lever arrangement to which the gimbal bearing 8b and the pressing plate 8b are attached, an area in which the displacement body 8 presses on the blood bag 12 is increased so that the individual blood components 16a, 16b and 16c are pressed out of the blood bag 12 even more reliably.

As such, the blood separation device 4 in accordance with the described modifications comprises the displacement body 8, which generates a pressing force Fp in the direction of the inner wall of the first chamber 4a by means of the centrifugal force Fz that is generated during a centrifugation process and/or by means of the spring force Ff provided by the spring 9. The blood bag 12 is thus, as shown in FIG. 2, in an inserted state, pressed against the inner wall of the first chamber 4a by the displacement body 8, so that the individual blood components 16a, 16b and 16c are pressed out of the blood bag 12.

Consequently, the blood separation device 4 in accordance with the invention does not require additional compressed air or hydraulic connection for generating the pressing force Fp. It is therefore possible to design the blood separation device 4 in accordance with the invention as an open container, hereinafter referred to as centrifuge inlet or inlet, the outer shape of which can be adapted to the inner shape of a receiving container of a conventional centrifuge. Furthermore, the inlet can be designed in such a way that it can be directly attached to a rotor of a centrifuge, so that no receiving container is required. The blood separation device 4 in accordance with the invention can therefore be used for centrifuges that already exist without a compressed air or hydraulic connection, thus avoiding the costly procurement of a special centrifuge requiring a high level of technical effort.

The use of the blood separation device 4 according to different embodiments is described below. It should be noted that the blood separation device 4 which is inserted into the receiving container is deflected 90° counter-clockwise due to the centrifugal force Fz that is generated, as the receiving container of a centrifuge is usually rotatably attached to a rotor of the centrifuge at the upper end in the middle. As a consequence, the first chamber 4a is above the second chamber 4b during centrifugation. As such, the lever arrangement of the displacement body 8 is pressed downwards during centrifugation. This arrangement offers the additional advantage that the weight of the lever arrangement in combination with the displaced centre of gravity of the lever arrangement ensures that the displacement body 8 presses the pressing force Fp towards the inner wall of the first chamber 4a. For the purpose of a simpler description, however, the directions are indicated below, as shown in the figures.

In the first embodiment, the blood bag 12 and the component bags 13 and 14 are arranged according to a so-called top-top specification. This means that the lines to the two component bags 13 and 14 are connected to the same end, e.g. a top end, of the blood bag 12. The blood bag 12 has an opening to which a line 12a is connected. This splits at a Y-branch into two lines 13a and 14a which are connected to a respective component bag 13 and 14.

A breaker valve is arranged in the line 12a so that the blood bag 12 is securely sealed in an initial state. The leucocytes of the blood 16 which are received in the blood bag 12 can be removed in advance by means of a leucocyte filter.

Figure 7:
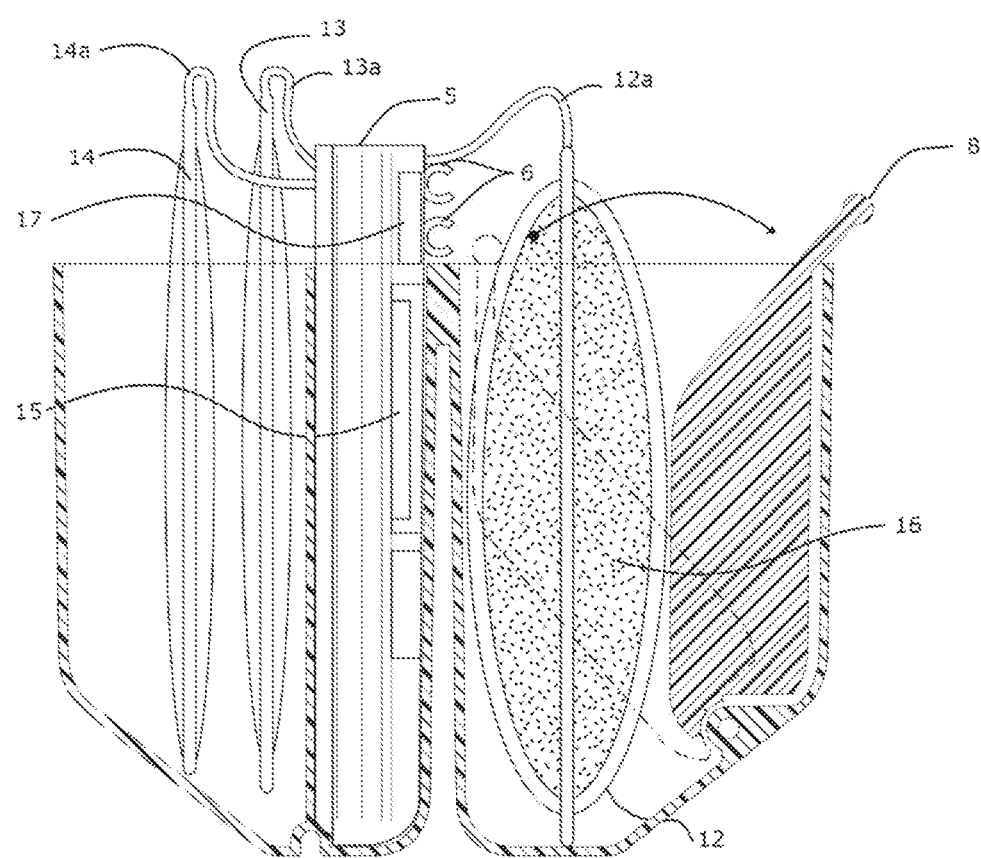
FIG. 7 shows the further modification of the blood separation device, in which the control unit as well as the blood bag and the two component bags are inserted, when used in accordance with the embodiment.

In FIGS. 2 and 7 the initial state is shown before the blood separation device 4 is inserted into the centrifuge. The blood bag 12 filled with the blood 16 to be separated and the intact breaker valve is inserted into the first chamber 4a by manually pushing the displacement body 8 to the right in the direction of the outer wall to which the displacement body 8 is rotatably attached. In FIGS. 2 and 7, the initial position of the displacement body 8 is shown by a dashed line, and the action of pressing to the rear is described by a curved solid arrow. After the displacement body 8 is released, it presses on the blood bag 12, wherein the pressing force Fp is higher in modifications with a spring force Ff in the initial state than in modifications without a spring force Ff. However, the intact breaker valve prevents blood 16, which has not yet been separated into the individual blood components, from being pressed out of the blood bag 12 and entering the component bags 13 and 14.

A control unit 5 is inserted into chamber 4c of the blood separation device 4 and is adapted to control a distribution of the blood components 16a, 16b and 16c to the component bags 13 and 14 by accordingly opening and closing valves in the individual lines 12a, 13a and 14a. For this reason, the control unit 5 comprises a microcomputer or other logic unit with a memory in which a corresponding software program is stored that controls the distribution of the blood components 16a, 16b, 16c. In the present modifications, the valves are formed by clamps, each of which is driven by means of an electric motor 15, which in turn, is controlled by the microcomputer of the control unit 5. The clamps as well as the associated electric motors 15 are also attached to the control unit 5 and the control unit 5 is advantageously operated by means of an independent power supply, such as batteries, so that no external connections are required.

This further reduces the technical complexity of the blood separation device 4 in accordance with the invention. Due to the low energy requirements of the electric motor and the microcomputer, one charge of the batteries is sufficient for several separation operations.

Lines 12a, 13a and 14a are inserted into the clamps and arranged at the inlet as follows. Line 12a, which is connected to the opening of the blood bag 12, is passed through a first clamp arranged in an upper portion of the control unit 5 protruding from the inlet. The first clamp is subsequently closed because the breaker valve is to be opened when the inlet is inserted into the centrifuge. This way, even after the breaker valve in the line 12a has been opened, unseparated blood 16 is prevented from entering one of the component bags 13 and 14 by the pressing force Fp which has already been applied. In this regard, it should be noted that all clamps into which lines 12a, 13a, 14a are to be respectively inserted are to be arranged and designed in such a way that any squeezing and/or kinking of the lines 12a, 13a, 14a accommodated therein is avoided in the event of an open clamp during the centrifugation process. This way, the flow path of lines 12a, 13a, 14a is reliably ensured.

Next, line 12a is guided down the outside of the inlet, which is shown close up in the figures, along the wall between the chamber 4c for the control unit 5 and the second chamber 4b, and is then guided along the outer bottom surface of the inlet to the other side of the inlet (towards the rear in the figures). In order to prevent the line from being squeezed or kinked when it is inserted into the receiving container of the centrifuge, a groove 7 is made in the outer surface of the inlet. When the line is guided this way, the Y-branch is located in the area of the centre of the outer bottom surface and this is to be inserted into a recess provided for this purpose. From there, two grooves 7 run along the outside of the inlet in order to receive the lines 13a and 14a, each individually, in a groove 7 provided for this purpose. In an upper section of the inlet, two holders 6 are arranged on the unit into which the lines 13a and 14a can be inserted. This way, lines 12a, 13a and 14a are fixed to the inlet and the circumferential grooves 7 and the recess for the Y-branch make it possible for the inlet to be inserted into the receptacle without one of the lines 12a, 13a, 14a being squeezed off or the Y-branch destroyed.

Alternatively or in addition to guiding the lines 12a, 13a, 14a on the blood separation device 4 itself, a guide plate 18 shown in FIGS. 13A and 13B can be used to guide the lines 12a, 13a, 14a. For this purpose, the lines 12a, 13a, 14a are inserted into the individual clips 18a of the guide plate 18 so that the lines are prevented from being kinked or squeezed during a centrifuging operation. The guide plate 18 also has two rails 18b which guide the lines 13a and 14a to the second chamber 4b in which the component bags 13 and 14 are housed. FIG. 14 shows a blood separation device 4 to which the guide plate 18 is attached. In this case, the guide plate 18 is attached to an upper portion of the inner wall of the first chamber 4a by a clamp, screw or other suitable retaining unit. The guide plate 18 is not limited to the embodiment or arrangement of the clips 18a that is shown and can be adapted to various blood bag systems with different lengths of line and line diameters in order to reliably prevent any kinking and/or squeezing of the lines 12a, 13a, 14a so that a flow path in the lines 12a, 13a, 14a is reliably ensured.

The lines 13a and 14a connected to the component bags 13 and/or 14 are passed through a second clamp, the second clamp being configured to receive both lines. The second clamp is further configured to open only one of the lines 13a and 14a, while respectively, the other line 13a or 14a is disconnected. Consequently, a blood component 16a, 16b, 16c can be transported into only one of the two component bags 13 and 14. However, it is not mandatory that this type is used for the clamp. For example, two individual clamps can also be used if it can be ensured that only one of the two clamps is open at the same time.

The component bags 13 and 14 are then arranged in the second chamber 4b, the breaker valve of the blood bag 12 is opened and the inlet is inserted with a positive lock into a receiving container of a centrifuge. The breaker valve can also be opened after the inlet has been inserted into the centrifuge container. By guiding lines 12a, 13a and 14a into grooves 7 on the outside of the inlet or into guide plate 18, it is possible to ensure that the individual lines 12a, 13a and 14a are not squeezed or damaged during insertion into the receiving container. In addition, the guiding of the lines 12a, 13a and 14a around the inlet or into the guide plate 18 prevents the individual lines 12a, 13a and 14a from protruding from the opening of the inlet, so that the risk of snagging with other parts of the centrifuge is reduced or avoided.

It should be noted that the displacement body 8 is already pressing on the blood bag 12, as described above. However, it is also ensured that no blood 16 enters either of the component bags 13 and 14 even after the breaker valve is broken open by the closed first clamp. When inserted into the centrifuge, the second clamp is configured so that line 13a to component bag 13 is open and line 14a to the other component bag 14 is interrupted.

Once one or more inlets have been inserted into the designated receptacles on the centrifuge rotor, the centrifuge is started. A centrifugal force Fz in the range of 1500 g to 3000 g is required to separate blood 16. For this, a speed in the range of 3000 rpm is to be set for typical centrifuges provided for blood bags 12. As described in further detail above, the blood separation device 4 is deflected approximately 90° counter-clockwise. The centrifugal force Fz consequently acts from top to bottom, as shown in the figures. After 5 to 15 minutes, this first phase of the centrifuging process, during which the blood is separated into the individual components, can be terminated.

Figure 3:
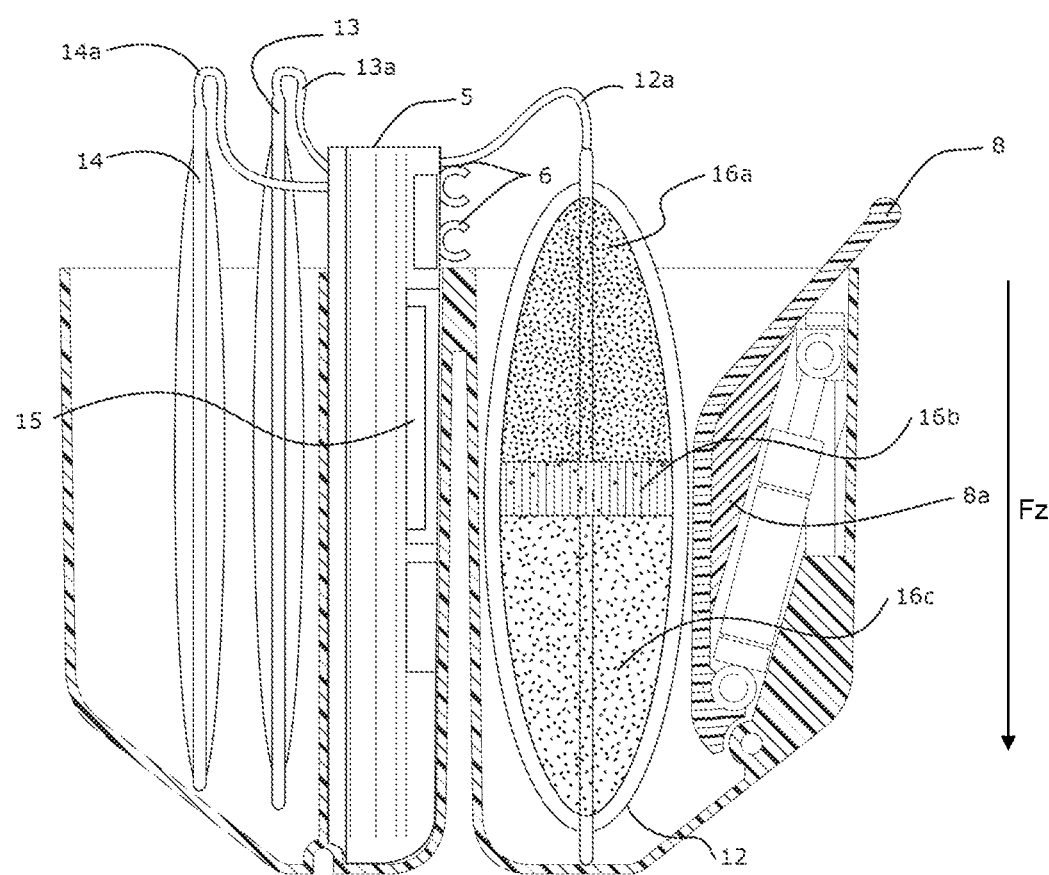
FIG. 3 shows the modification of the blood separation device when used in accordance with the embodiment after the completion of a first phase of a centrifugation process in which blood is separated into individual components.
Figure 8:
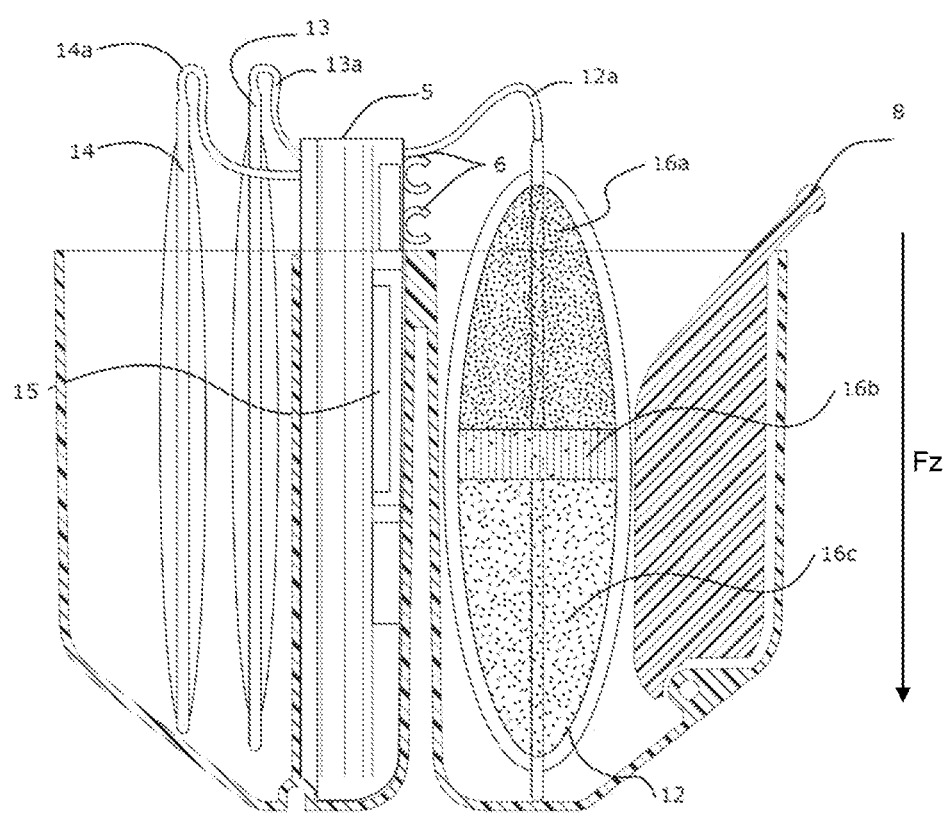
FIG. 8 shows the further modification of the blood separation device when used in accordance with the embodiment after the completion of the first phase of the centrifugation process in which the blood is separated into the individual components.

During the first phase of the centrifuging process, the blood 16 is transferred into the individual blood components 16a, 16b and 16c, as shown in FIGS. 3 and 8.

The individual blood components 16a, 16b and 16c are arranged according to their specific gravity in the direction of the centrifugal force Fz, whereby blood components 16a, 16b and 16c with a higher specific gravity are arranged further out, as shown further down in the figures. The direction in which the individual blood components 16a, 16b and 16c are arranged is also referred to as the separation direction. In particular, the individual blood components in the present embodiment are blood plasma 16a, buffy coat 16b and erythrocytes 16c.

Preferably, the blood separation device 4 in accordance with the present invention comprises a position sensor designed to determine the position of the buffy coat 16c in the blood bag 12. As such, it is possible to determine the haematocrit of the separated blood 16. The position sensor is designed, for example, as an optical sensor and is also used for an embodiment that is described further below.

After completion of the first phase of the centrifugation process, the centrifuge is adjusted in a second phase so that there is a lower centrifugal force Fz than during the first phase. Preferably, the second phase is a phase in which the centrifuge is adjusted so that there is a predetermined centrifugal force Fz. It should be noted that the centrifugal force Fz during the second phase is smaller than the centrifugal force Fz during the first phase. Alternatively, the second phase may be the petering out of a centrifuge rotor.

During the second phase, the blood components 16a, 16b and 16c are transferred to the respective component bags 13 and 14 so that they are available for examination and/or therapeutic measures. For this reason, the first clamp is opened first and the displacement body 8, which is already pressing on the blood bag 12 with the pressing force Fp, pushes the blood components 16a, 16b and 16c out of the blood bag 12 in the direction of separation. Transferring blood components 16a, 16b and 16c during the second phase also offers the advantage of avoiding any re-mixing of the individual blood components 16a, 16b and 16c when the blood bag 12 is once again stored in a vertical orientation for a longer period of time, as is necessary, for example, when using a separate blood separation device.

Figure 4:
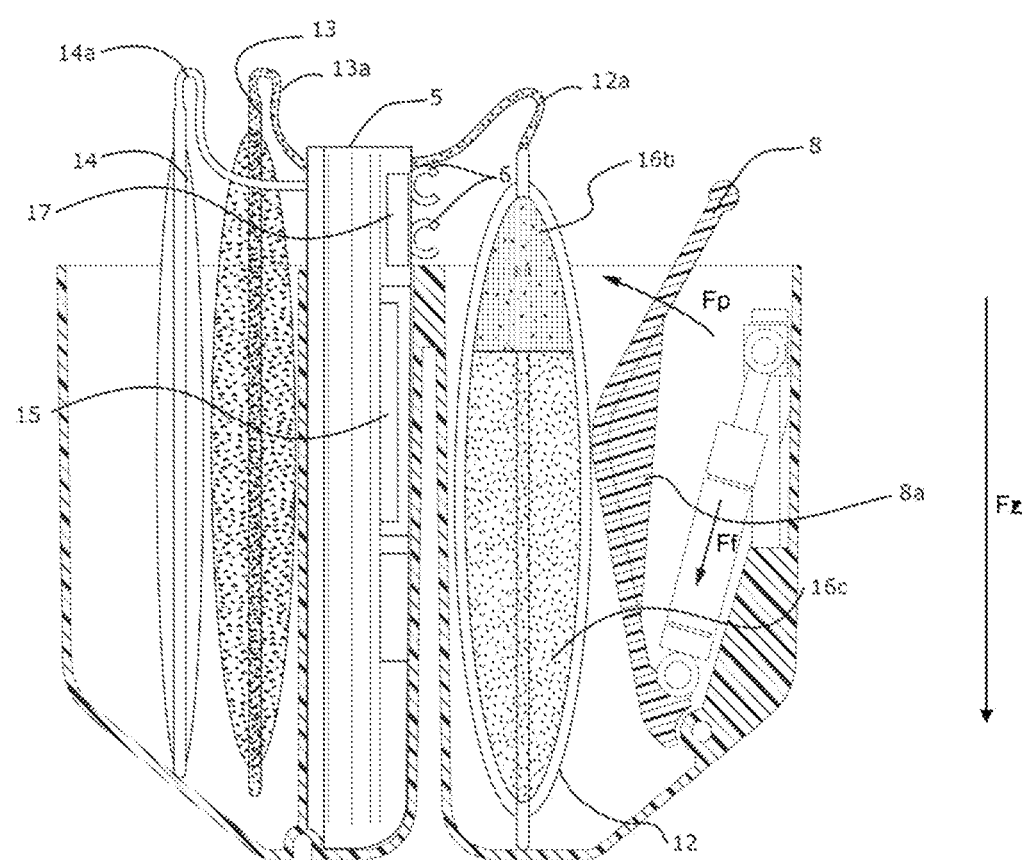
FIG. 4 shows the modification of the blood separation device when used in accordance with the embodiment in which one of the blood components has passed from the blood bag via a line into one of the component bags.
Figure 9:
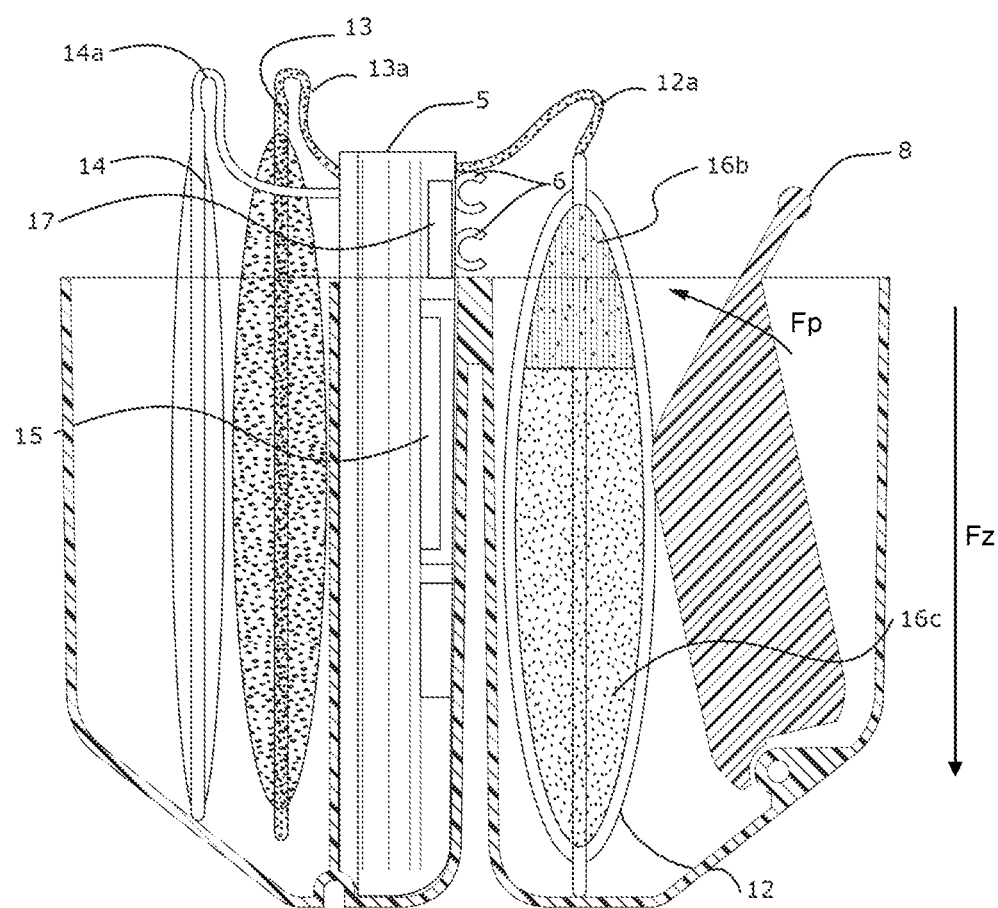
FIG. 9 shows the further modification of the blood separation device when used in accordance with the embodiment in which one of the blood components has passed from the blood bag via a line into one of the component bags.

Accordingly, plasma 16a is initially forced out of blood bag 12, as shown in FIGS. 4 and 9, and enters component bag 13 which is provided for plasma via lines 12a and 13a.

The control unit includes a sensor 17 that determines whether a blood component associated with a clamp has been fully pushed out of the blood bag 12 and as such, also determines that a blood component has fully entered the component bag 13 and 14 provided for it. In the present modifications, a colour sensor is used for this purpose. Consequently, the sensor 17 detects a colour change occurring in the region of the opening of the blood bag 12, thereby enabling the control unit 5 to determine, for example, that the yellowish plasma 16a has been completely pressed out of the blood bag 12. If using the sensor 17, the control unit 5 determines that the plasma 16a is fully pushed out of the blood bag 12, it switches the second clamp so that the line 14a is open and the line 13a is closed. The first clamp, through which line 12a is routed, remains open so that there is a flow path from the opening of the blood bag 12 via lines 12a and 14a to the opening of the second component bag 14.

Figure 5:
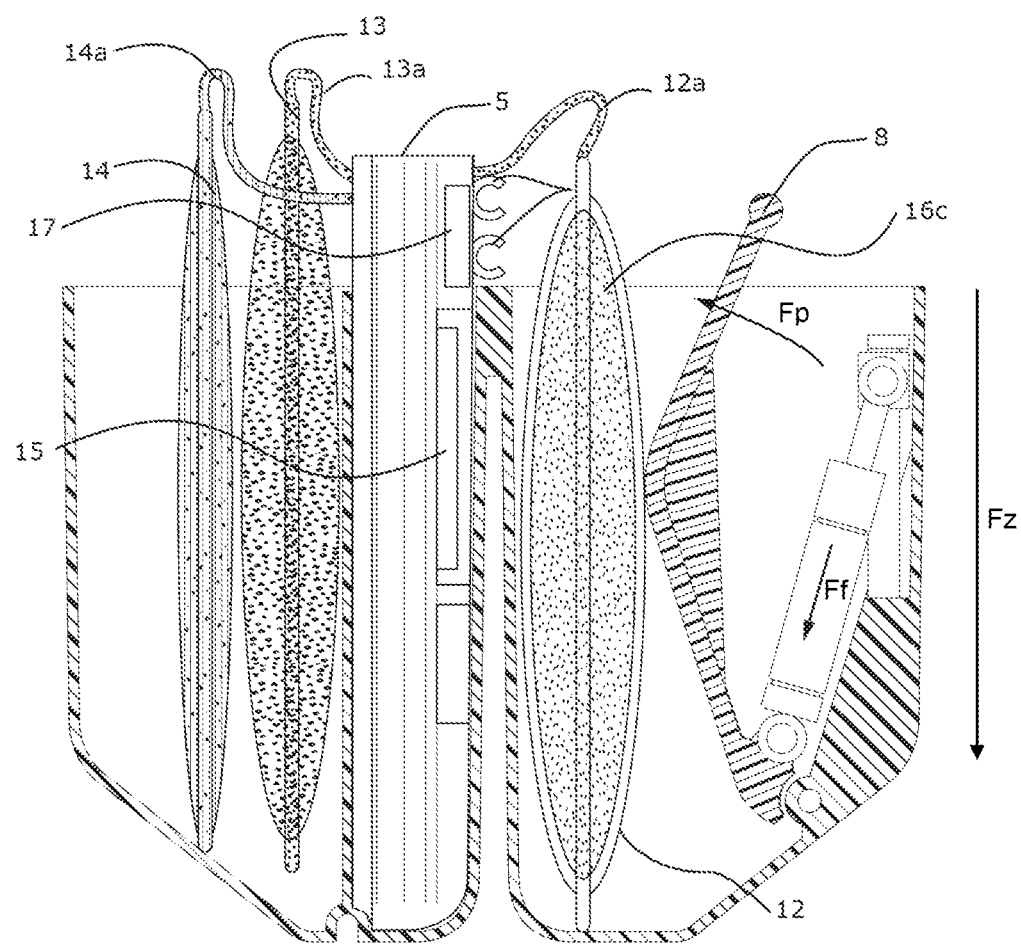
FIG. 5 shows the modification of the blood separation device when used in accordance with the embodiment, in which another blood component has passed from the blood bag via another conduit into another component bag.
Figure 10:
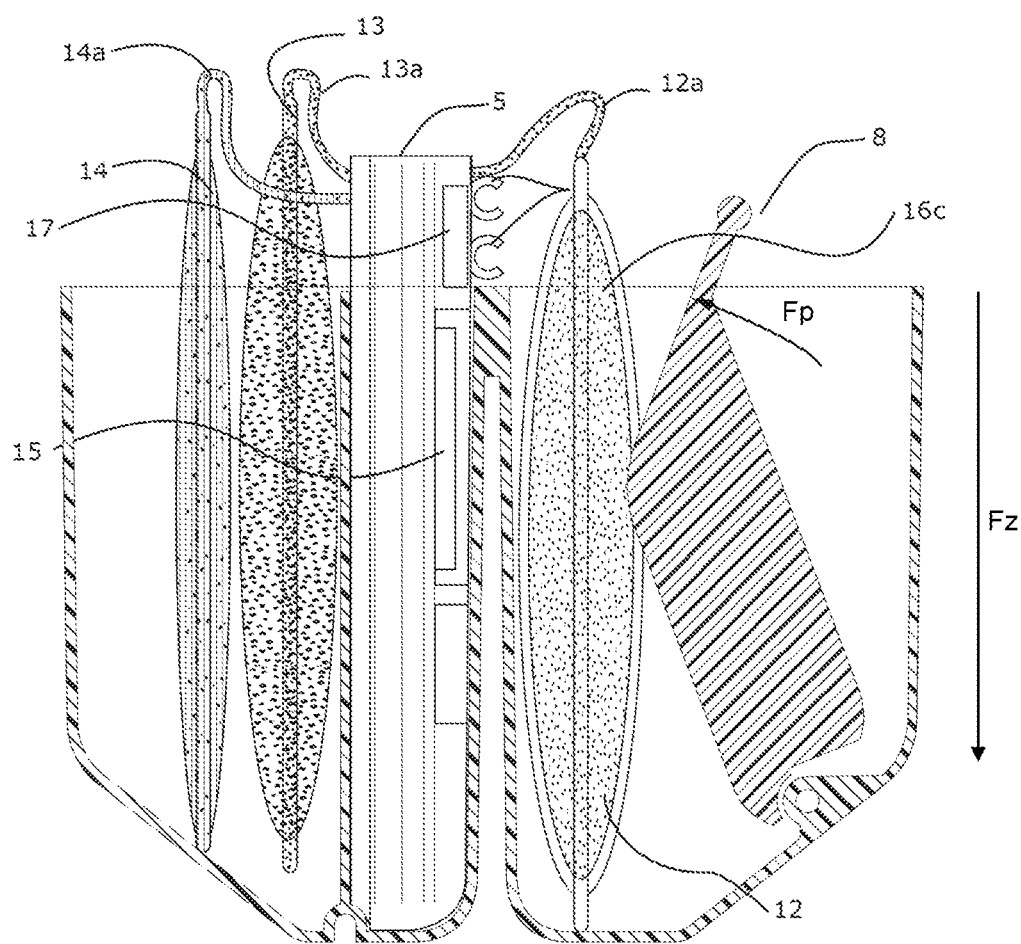
FIG. 10 shows the further modification of the blood separation device when used in accordance with the embodiment, in which another blood component has passed from the blood bag via another line into another component bag.

Due to the centrifugal force Fz and/or the spring force Ff which continues to be present during the second phase, the pressing force Fp is further generated substantially perpendicular to the direction of the centrifugal force Fz. This presses on the blood bag 12, and the buffy coat 16b is pressed out of the blood bag 12, as can be seen in FIGS. 5 and 10, and in this way, enters the second component bag 14. When, by means of the sensor 17, the control unit 5 determines that the buffy coat has completely entered the component bag 13 provided for this purpose, it closes the first valve so that the line 12a is interrupted. Consequently, the erythrocytes 16a are no longer pushed out of the blood bag 12 and the different blood components 16a, 16b and 16c are in the blood bag 12 as well as the intended component bags 13 and 14, and these can be further processed or examined individually.

It is not mandatory to use the sensor 17 to determine whether the plasma 16a or buffy coat 16b is completely ejected out of the blood bag 12. Alternatively, the control unit 5 can also be used to determine the amount of separated blood components 16a and 16b that are ejected out of the blood bag 12. In each case an empirically determined time duration t1 is used. The time duration t1 is to be determined separately for the individual blood components 16a or 16b.

Preferably, the centrifuge is set so that a defined centrifugal force Fz is present. This way, the time period t1 can be set independently of the type of centrifuge, i.e. independently of a rotor diameter and a speed.

The defined centrifugal force Fz is detected by an acceleration sensor mounted on the blood separation device 4 and the control unit 5 obtains the value of the centrifugal force Fz from the acceleration sensor. The acceleration sensor is preferably attached to the control unit 5 for this purpose. The acceleration sensor attached to the blood separation device 4 thus provides the advantage that the defined centrifugal force Fz can be set reliably and independently of the type of centrifuge. When the defined centrifugal force Fz is reached during the second phase of the centrifugation process, the control unit 5 can automatically start a transfer of the individual blood components 16a and 16b into the respective component bags 13 and 14.

In order to set the predetermined centrifugal force Fz, the blood separation device 4 has a remote control unit provided outside of the centrifuge, which is capable of performing bidirectional wireless communication with the control unit 5. For this purpose, the control unit 5 is also equipped with a unit for performing bidirectional wireless communication with the remote-control unit. The remote control unit is preferably a smartphone, a tablet computer or a similar portable unit, and the wireless communication is performed via a wireless LAN connection or some similar connection. Consequently, the value of the centrifugal force Fz detected by the acceleration sensor can be transmitted from the control unit 5 to the remote control unit and the speed of the centrifuge can be changed accordingly so that the predetermined centrifugal force Fz occurs.

Then, when the predetermined centrifugal force Fz acts, the transfer of the blood components 16a and 16b can either be started manually by using the remote control unit or automatically by using the control unit 5. Consequently, the use of the acceleration sensor and the remote control unit allows for the blood separation device 4 in accordance with the invention to also be used for simple centrifuges without a unit for measuring the centrifugal force Fz.

After the plasma 16a and the buffy coat 16b have been pressed into the respective component bags 13 and 14, the clamps, especially the first clamp, are closed to prevent any further ejection of the erythrocytes 16c from the blood bag 12.

Once the rotor of the centrifuge has stopped, the inlet can be removed from the receiving container and the blood bag 12 containing the red cells 16c and the two component bags 13 and 14 containing the plasma 16a and/or the buffy coat 16b can be removed from the inlet.

Accordingly, the present invention offers the advantage that the individual blood components 16a, 16b and 16c are already available in separate containers when the centrifuge stops. Compared to conventional working methods in which the blood components 16a, 16b and 16c are only separated after the centrifuge has stopped, the blood separation device 4 in accordance with the invention provides the advantage that the blood components 16a, 16b and 16c are not mixed in the time between centrifugation and the ejection of the individual blood components 16a, 16b and 16c using a separate device. In addition, compared to a working method in which the blood components 16a, 16b and 16c are separated by a separate device, fewer working steps are required, thus saving time.

In the following section, a use of the blood separation device 4 in accordance with the invention is described according to another embodiment. One of the modifications of the blood separation device 4 when used in accordance with the other embodiment is shown by way of example in FIG. 11. However, it should be noted that any other modification of the blood separation device 4 according to the invention can be used in accordance with this embodiment. In this embodiment, the blood bag 12 and the component bags 13 and 14 are arranged according to a so-called top-bottom specification. This means that the two component bags 13 and 14 are connected at different ends, at a top end and/or a bottom end, of the blood bag 12. The blood bag 12 therefore has two openings to which the lines 13a and/or 14a are directly connected. As such, line 12a and the Y-branch are not required in this configuration. A breaker valve is arranged in each of the lines 13a and 14a so that the blood bag 12 is securely closed in an initial state.

Figure 11:
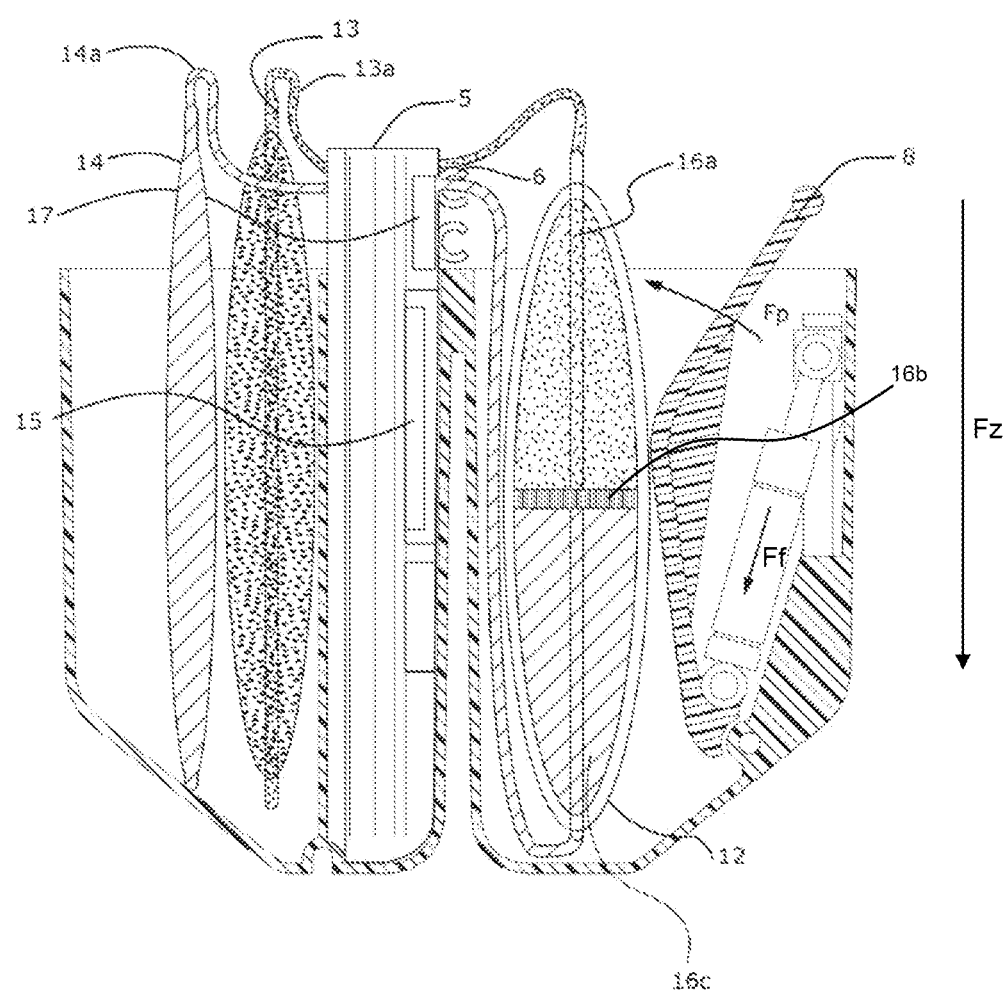
FIG. 11 shows one of the modifications of the blood separation device when used in accordance with a further embodiment in which a first clamp and a second clamp are alternately opened so that a blood component and/or another blood component correspondingly enter a respective component bag via respective lines.

The blood bag 12 and the component bags 13 and 14 are inserted into the inlet before centrifugation, as shown in FIG. 11, with the blood bag 12 in the first chamber 4a and the two component bags 13 and 14 in the second chamber 4b. In this embodiment, as mentioned above, one opening of the blood bag 12 connected to the component bag 13 via one line 13a is arranged at the top and another opening of the blood bag 12 connected to the component bag 14 via the other line 14a is arranged at the bottom. In order to control the distribution of the blood components 16a, 16b and 16c, the lines 13a and 14a are inserted into a first clamp and/or a second clamp, which interrupt a flow path in lines 13a and 14a prior to centrifugation. Subsequently, the two breaker valves in lines 13a and 14a can be opened and the inlet can be introduced into the receiving container of the centrifuge. As described above, the breaker valves can also only be opened after the inlet has been inserted into the receiving container.

As in the embodiment described above, the blood is separated into the individual blood components, plasma 16a, buffy coat 16b and erythrocytes 16c, during the first phase of the centrifugation process.

In particular, a separation of the individual components 16a, 16b, 16c between the component bags 13 and 14 and the blood bag 12 during the second phase of the centrifugation process differs from the previously described embodiment. The displacement body 8 presses on the blood bag 12 by means of the centrifugal force Fz and/or the spring force Ff and the first clamp, in which the line 13a is inserted, and the second clamp, in which the line 14a is inserted, are opened in succession. This way, the plasma 16a first passes through the opening at the upper end of the blood bag 12 via the line 13a into the component bag 13 and then the erythrocytes 16c pass through the opening at the lower end of the blood bag 12 via the other line 14a into the other component bag 14. It is also possible to first transfer the erythrocytes 16c and then the plasma 16a into the respective component bags 13 and 14. In contrast to the use in accordance with the first embodiment, the buffy coat 16b remains in the blood bag 12 and the erythrocytes 16c are transported into the component bag 14. In this embodiment, sensors 17 are used to determine whether the plasma 16a and the erythrocytes 16c are completely ejected out of the blood bag 12. For this purpose, in addition to the sensor 17 in the region of the upper opening of the blood bag 12, a further sensor 17 is to be arranged in the vicinity of the lower opening of the blood bag 12. Alternatively, it is possible to once again determine a time period t1 which is required to eject the plasma 16a or the erythrocytes 16c out of the blood bag. The time t1 is to be determined separately for the individual blood components 16a and/or 16c. Preferably, the time duration t1 is once again determined for a predetermined centrifugal force Fz, which is determined during the second phase of the centrifugation process with the aid of the acceleration sensor.

Preferably, the control unit 5 alternately controls the first clamp and the second clamp in order to keep the buffy coat 16b in a predetermined area of the blood bag 12. The position of the buffy coat 16b is thereby determined with the aid of the position sensor described above. This way, the buffy coat 16b is prevented from being pushed from the position at which it is located, to one of the two openings following the completion of the centrifugation process. This way, contamination with buffy coat 16b on the inner wall of the blood bag 12, which is subsequently present in the plasma 16a and/or the erythrocytes 16c, can be reduced compared to a case in which the buffy coat 16b reaches the vicinity of the openings at the upper and/or lower ends of the blood bag 12, when one of the two blood components 16a and 16c is completely ejected. As such, this procedure, in which the blood bag 12 and the component bags 13, 14 are used in accordance with a top-bottom arrangement and the plasma 16a and the erythrocytes 16c are ejected by alternately opening the clamps, offers the advantage that a leucocyte filter is not necessarily required, since impurities are reduced by the buffy coat 16b. After the plasma 16a and red cells 16c are ejected into the respective bags 13 and/or 14, the clamps in which the lines 13a and 14a are received are closed to prevent the buffy coat 16b from being ejected from the blood bag 12.

After the rotor of the centrifuge is stopped, the inlet can be removed from the receiving container provided for this purpose and the two component bags 13 and 14 containing the plasma 16a and/or the erythrocytes 16c and the blood bag 12 containing the buffy coat 16b can be removed from the inlet. Similar to the embodiment above, this embodiment provides the advantage that the components are separated between the individual component bags 13 and 14 and the blood bag 12 after completion of the centrifugation process. As such, re-mixing of the blood components 16a, 16b, 16c is avoided during the period up until they are introduced into an external separation device.

The invention claimed is:

1. A blood separation device for separating blood into a plurality of blood components by a centrifugal force generated during a centrifuging process in a centrifuge, the blood separation device comprising:
 a first chamber for receiving a blood bag filled with the blood, the blood separating into the plurality of blood components by the centrifugal force in such a way that each of the plurality of blood components is located—as seen in a direction of the centrifugal force—in a separate section of the blood bag according to its specific weight after completion of a first phase of the centrifuging process,
 a second chamber for receiving at least one component bag that is provided for filling with one of the plurality of blood components,
 the at least one component bag comprising an inlet opening that is connected to an outlet opening of the blood bag via a line in which a controllable valve is arranged,
 a displacement body being arranged in the first chamber and exerting a pressing force onto the blood bag which is directed substantially perpendicular to the direction of the centrifugal force, wherein the displacement body is shaped in order to generate the pressing force by the centrifugal force and/or by a spring force, and a control unit, which during a second phase of the centrifuging process opens the controllable valve until said one of the plurality of blood components has passed into the at least one component bag as a result of the pressing force of the displacement body.

2. The blood separation device in accordance with claim 1, wherein the displacement body has a lever arrangement which redirects part of the centrifugal force and/or the spring force to generate the pressing force.

3. The blood separation device in accordance with claim 2, wherein the lever arrangement is rotatably mounted on a wall of the first chamber on an axis of rotation.

4. The blood separation device in accordance with claim 3 further comprising a spring for generating the spring force, wherein a first end of the spring is attached to the wall of the first chamber and a second end of the spring is attached to the lever arrangement.

5. The blood separation device in accordance with claim 3, wherein an upper portion of the lever arrangement is angled at a predetermined angle towards the wall of the first chamber.

6. The blood separation device in accordance with claim 2, wherein a gimbal bearing and a pressing plate are attached to the lever arrangement.

7. The blood separation device in accordance with claim 1, wherein the control unit comprises at least one sensor for detecting an amount of said one of the plurality of blood components that is ejected out of the blood bag.

8. The blood separation device according to claim 7, wherein the control unit is configured to determine the amount of said one of the plurality of blood components that is ejected out of the blood bag, and wherein, an empirically determined time duration is used.

9. The blood separation device in accordance with claim 1, further comprising an acceleration sensor for detecting the centrifugal force.

10. The blood separation device in accordance with claim 1, further comprising a remote control unit for performing bidirectional communication with the control unit.

11. The blood separation device in accordance with claim 1, wherein the controllable valve is an electric motor driven clamp.

12. The blood separation device in accordance with claim 1, wherein the first chamber, the second chamber, and the control unit are arranged in an inlet.

13. The blood separation device in accordance with claim 12, wherein the inlet is removable so that the blood bag and the at least one component bag are insertable into the inlet when the inlet is removed and/or is removable when blood separation is complete.

14. The blood separation device in accordance with claim 1, further comprising a guide plate for guiding the line.

15. The blood separation device in accordance with claim 1, wherein the displacement body is configured to generate the pressing force solely by the centrifugal force and/or by a spring force.

16. The blood separation device in accordance with claim 2, wherein the displacement body is configured to generate the pressing force solely by the centrifugal force and/or by a spring force.

* * * * *